US009061964B2

(12) United States Patent
Sakuma et al.

(10) Patent No.: US 9,061,964 B2
(45) Date of Patent: *Jun. 23, 2015

(54) METHOD FOR PRODUCING TERTIARY AMINE (71) Applicant: Kao Corporation, Tokyo (JP)

(72) Inventors: Yasumitsu Sakuma, Wakayama (JP);
Wataru Nomura, Wakayama (JP);
Goshi Yamamoto, Wakayama (JP);
Takeshi Narushima, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/327,936

(22) Filed: Jul. 10, 2014

(65) Prior Publication Data

US 2014/0323764 A1  Oct. 30, 2014

Related U.S. Application Data

(63) Continuation of application No. 13/996,311, filed as application No. PCT/JP2011/079337 on Dec. 19, 2011, now Pat. No. 8,877,978.

(30) Foreign Application Priority Data

Dec. 21, 2010  (JP) .................................. 2010-284201
Dec. 21, 2010  (JP) .................................. 2010-284202

(51) Int. Cl.
*C07C 209/22* (2006.01)
*C07C 209/70* (2006.01)
*C07C 209/16* (2006.01)
*B01J 23/72* (2006.01)
*B01J 35/04* (2006.01)
*B01J 29/068* (2006.01)
*B01J 29/072* (2006.01)

(52) U.S. Cl.
CPC ............. *C07C 209/22* (2013.01); *B01J 29/072*
(2013.01); *B01J 35/04* (2013.01); *C07C 209/16*
(2013.01); *B01J 23/72* (2013.01); *B01J 29/068*
(2013.01); *B01J 2229/186* (2013.01); *B01J*
*2229/38* (2013.01); *B01J 2229/42* (2013.01);
*C07C 209/70* (2013.01)

(58) Field of Classification Search
None
See application file for complete search history.

(56) References Cited

U.S. PATENT DOCUMENTS

| 2,953,601 | A | 9/1960 | Whitaker et al. |
| 4,859,642 | A | 8/1989 | Hoelderich et al. |
| 5,696,294 | A | 12/1997 | Abe et al. |
| 6,123,323 | A | 9/2000 | Yoneda et al. |
| 7,351,866 | B2 | 4/2008 | Hirota et al. |
| 7,615,666 | B2 | 11/2009 | Nishimura et al. |
| 8,338,647 | B2 | 12/2012 | Nomura et al. |
| 8,877,978 | B2 * | 11/2014 | Sakuma et al. ............... 564/479 |
| 2008/0004472 | A1 | 1/2008 | Nishimura et al. |
| 2010/0160673 | A1 | 6/2010 | Bruns et al. |
| 2010/0217044 | A1 | 8/2010 | Nomura et al. |

FOREIGN PATENT DOCUMENTS

| CN | 101612591 A | 12/2009 |
| EP | 1738826 A1 | 1/2007 |
| JP | 61-291044 A | 12/1986 |
| JP | 10-118473 A | 5/1998 |
| JP | 10-146523 A | 6/1998 |
| JP | 2008-94800 A | 4/2008 |
| JP | 2009-073754 A | 4/2009 |
| JP | 2010-013422 A | 1/2010 |
| JP | 2010-110673 A | 5/2010 |
| JP | 2010-143899 A | 7/2010 |
| WO | WO 2005/035122 A1 | 4/2005 |

OTHER PUBLICATIONS

Chinese Office Action and Search Report for Chinese Application No. 201180061796.6, dated Mar. 27, 2014, with a partial English translation.
English translation of JP-2010-013422-A, published Jan. 21, 2010.
International Preliminary Report on Patentability, issued on Jul. 2, 2013, for International Application No. PCT/JP2011/079337.
International Search Report issued in PCT/JP2011/079337, mailed on Mar. 19, 2012.
Kawakami et al., "Kagaku Kougaku Ronbunshu" (Collection of Chemical Engineering Papers), vol. 13, 1987, pp. 318-324.
Office Action for German Application No. 112011104476.3, dated Oct. 14, 2013, including a partial English translation.
Okabe et al., "Development of Catalysts for Direct Amination of Aliphatic Alcohols," Studies in Surface Science and Catalysis, vol. 44, Dec. 31, 1989, pp. 299-306.
Patrick, Jr. et al., "Residence Time Distribution in Three-Phase Monolith Reactor", AIChE Journal, vol. 41, No. 3, Mar. 1995, pp. 649-657.

(Continued)

*Primary Examiner* — Brian J Davis
(74) *Attorney, Agent, or Firm* — Birch, Stewart, Kolasch & Birch, LLP (57) ABSTRACT

The present invention discloses the method for producing a tertiary amine, using the column reactor packed with catalyst layers, containing supplying a liquid and a gaseous raw materials from the bottom of the column, reacting these raw materials in the column, and discharging the product from the top of the column, wherein the column reactor includes two or more honeycomb catalyst layers as the catalyst layers, one or more spaces between each honeycomb catalyst layer, and one or more rectifying sections that prevents a partial or whole back flow of the raw materials, arranged in each space without contacting with the honeycomb catalyst layer.

30 Claims, 4 Drawing Sheets

(56) References Cited

OTHER PUBLICATIONS

Sederman et al., "MRI strategies for characterising two-phase flow in parallel channel ceramic monoliths", Catalysis Today, vol. 128, 2007, pp. 3-12.

Thulasidas et al., "Dispersion during bubble-train flow in capillaries", Chemical Engineering Science, vol. 54, 1999, pp. 61-76.

Written Opinion issued in PCT/JP2011/079337, mailed on Mar. 19, 2012.

* cited by examiner

METHOD FOR PRODUCING TERTIARY AMINE

CROSS-REFERENCE TO RELATED APPLICATIONS

This application is a Continuation of co-pending application Ser. No. 13/996,311 filed on Jun. 20, 2013, which is a National Phase of PCT International Application No. PCT/JP2011/079337 filed on Dec. 19, 2011, which claims priority under 35 U.S.C. §119(a) to Patent Application No. 2010-284201 filed in Japan on Dec. 21, 2010 and Patent Application No. 2010-284202 filed in Japan on Dec. 21, 2010. All of the above applications are hereby expressly incorporated by reference into the present application.

FIELD OF THE INVENTION

The present invention relates to a method for efficiently producing a corresponding tertiary amine with a honeycomb catalyst from an alcohol and a primary or secondary amine.

BACKGROUND OF THE INVENTION

Aliphatic amines produced with beef tallow, coconut oil, palm oil, and the like are important intermediates for domestic and industrial applications. Aliphatic tertiary amines have a wide variety of applications such as a fabric softener, an antistatic agent, a rinsing agent, and other detergent through modification into a quaternary ammonium salt, an amphoteric surfactant, or the like.

Arts of production of a tertiary amine, in particular a method for efficiently producing a tertiary amine, have been explored by the process of reacting an alcohol and a primary or secondary amine in the presence of a catalyst.

JP-A 2008-94800 discloses use of a film catalyst containing a catalyst metal and a film supporting the catalyst metal on the surface thereof. The method does not have to stir or separate the catalyst by filtration, compared with a reaction in an alcohol containing a powder catalyst dispersed therein. JP-A 2008-94800 describes that reactive gas is supplied to a reactor through a feed opening having a diameter D of 0.3 to 200 mm.

JP-A 61-291044, published on 1986, discloses a method for facilitating mass transfer and heat exchange by constructing each honeycomb catalyst layer with a honeycomb catalyst and a static mixing element inserted in the catalyst. The static mixing element is expected to facilitate mixing of gas and liquid between honeycomb catalyst layers.

However, as described in Koei Kawakami et al., Kagaku Kougaku Ronbunshu (Collection of Chemical Engineering Papers) 13 (1987) 318; Patrick, R. H. et al., AIChE. J. 41 (1995) 649; Thulasidas, T. C. et al., Chem. Eng. Sci. 54 (1999) 61; and Sederman, A. J. et al., Catal. Today 128 (2007) 3, in case of conducting a reaction between gas and liquid flowing upward in parallel through a monolith catalyst in a reaction column, a residence time distribution in the reaction column is same to that in a complete mixing reaction system. A part of flowing gas and liquid may take a short pass, and another part may remain in the reaction column for a long time, causing an overreaction. It is also described that the residence time distribution cannot be improved from the state same to a complete mixing reaction system just by increasing a gas dispersibility.

US-A 2008/0004472 discloses production of a tertiary amine by reacting an alcohol and a primary or secondary amine in the presence of a film catalyst. JP-A 10-118473, published on 1998, and JP-A 10-146523, published on 1998, disclose a gas-liquid dispersion device generating a gas-liquid distribution phase.

SUMMARY OF THE INVENTION

The present invention relates to a method for producing a tertiary amine, including supplying liquid and gaseous raw materials from the bottom of a column reactor, packed with catalyst layers, reacting the raw materials in the column, and discharging a product from the top of the column, wherein the column reactor includes two or more honeycomb catalyst layers as the catalyst layers, a space between two or more honeycomb catalyst layers, and rectifying sections that are means for preventing back flow of part or the whole of the liquid and gaseous raw materials, arranged in the space without contacting with the honeycomb catalyst layer.

DETAILED DESCRIPTION OF THE INVENTION

None of references described above discloses an efficient method of conducting a reaction between gas and liquid flowing upward in parallel through a monolith catalyst.

The present invention provides an efficient method for producing a tertiary amine using an upflow column reactor in which raw materials are supplied from the bottom and a product and the like are discharged from the top, containing reacting a liquid and a gaseous raw materials in the presence of a honeycomb catalyst.

According to the present invention, during reacting in an upflow column reactor in which a liquid and a gaseous raw materials are supplied from the bottom and a product and the like are discharged from the top, back mixing from the lower to the upper stream (from the top to the bottom of the column) is prevented to suppress overreactions which are caused by a short pass or an increasing residence time of gas and liquid in the honeycomb catalyst layers.

Accordingly, whole cells (narrow tubular channels) in a honeycomb catalyst layer can be efficiently used, and an amount of a gaseous amine supplied can be reduced. A target tertiary amine therefore can be efficiently produced.

The present invention provides an efficient method for producing a tertiary amine through a reaction between a liquid and a gaseous raw materials.

In Figures, the numbers are assigned as follows.
1: column reactor
2: gas feeder
2A: supply nozzle
3: buffer tank 4: packed column
5: primary or secondary amine storage tank
6: hydrogen tank
11: column
12a to 12e: honeycomb catalyst layers
13a to 13e: spaces
14a to 14e: rectifying sections
31, 32, 33, and 34: valves
35: circulation pump <Column Reactor>

Figure 1:
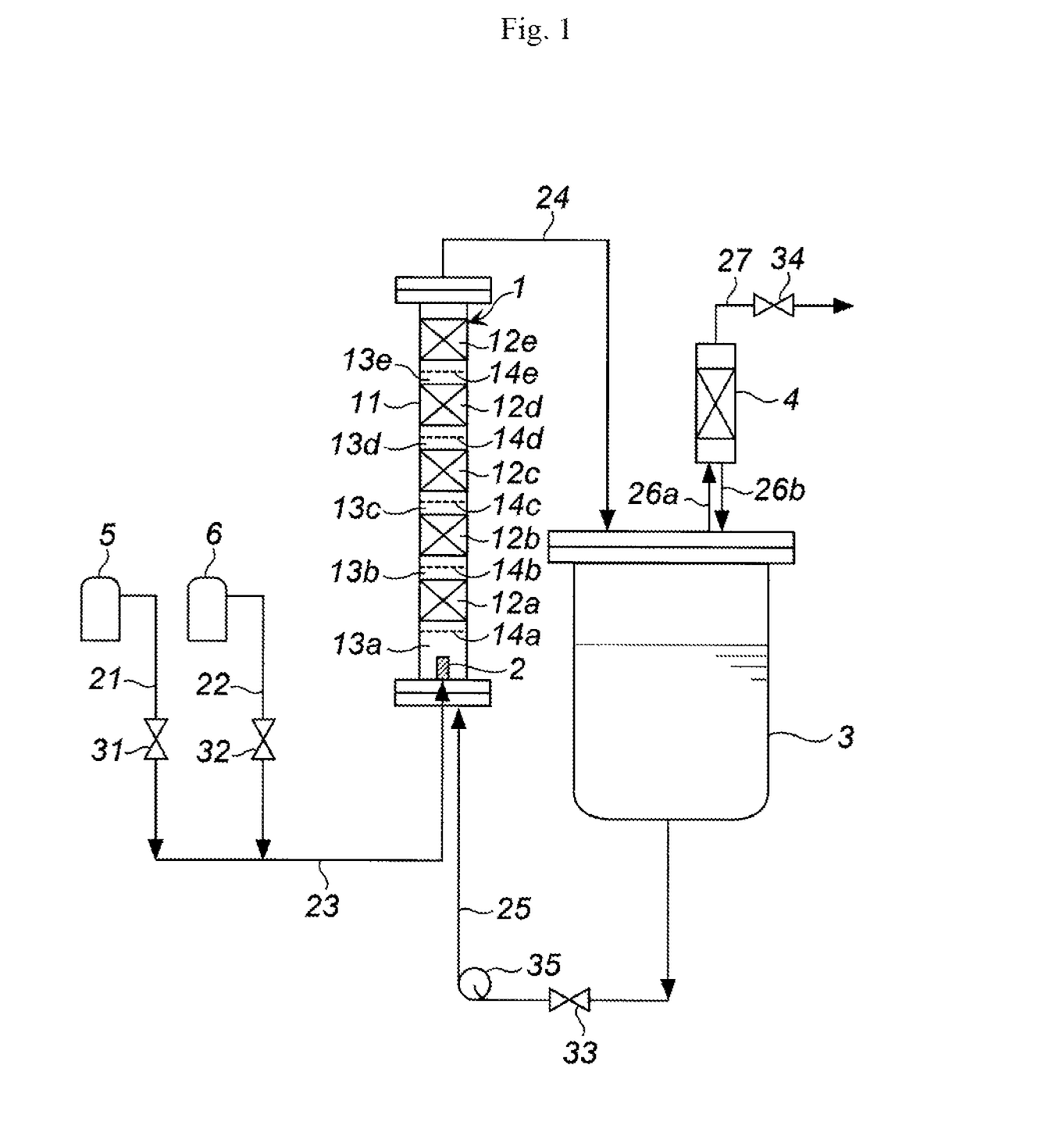
FIG. 1 shows a schematic flow diagram of production equipment for conducting the method of the present invention.
Figure 2:
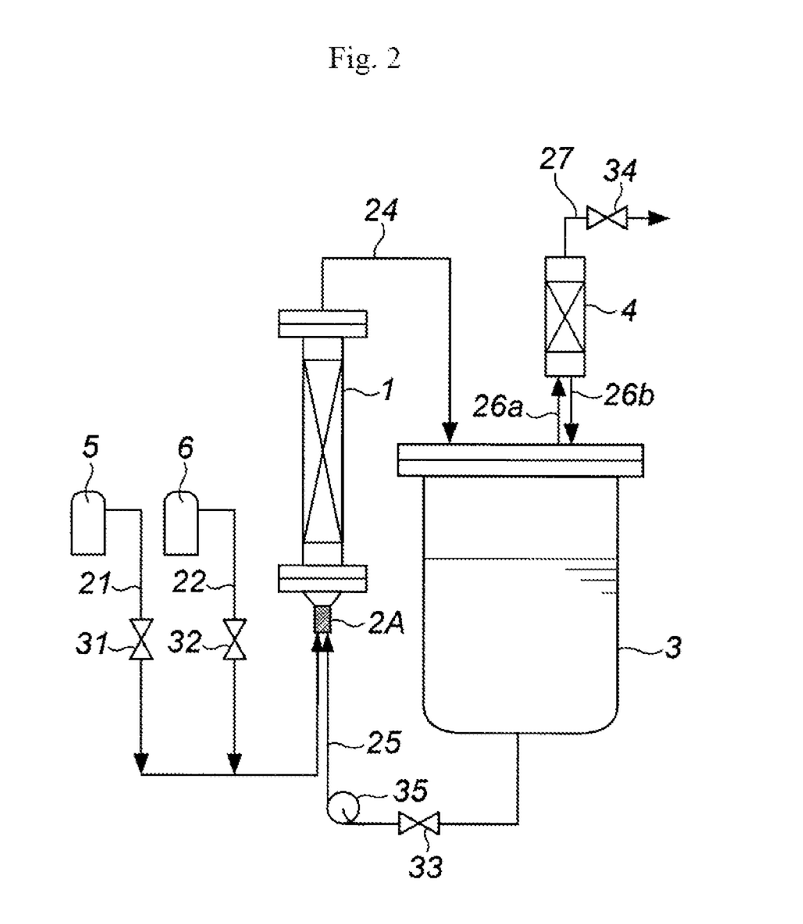
FIG. 2 shows a schematic flow diagram of production equipment in another embodiment for conducting the method of the present invention.

An example of the column reactor used in the method of the present invention will be described with reference to FIGS. 1 and 2. Column reactors 1 in FIGS. 1 and 2 are equal to each other, except that a feeding device (gas feeder) 2 in FIG. 1 is different from a feeding device (supply nozzle that blows a mixture of a liquid and a gaseous raw materials) 2A in FIG. 2. In FIG. 2, the internal structure of the column reactor 1 is not shown.

The column reactor 1 includes a column 11 packed with five honeycomb catalyst layers 12a to 12e in the vertical direction.

The number of honeycomb catalyst layers is at least two, preferably not less than three, and more preferably not less than four. The number of layers may be ten or more or twenty or more.

One honeycomb catalyst layer may be a single layer of formed catalyst, or plural layers of honeycomb catalyst layers in combination.

There are spaces 13a to 13e below the honeycomb catalyst layer 12a and each between honeycomb catalyst layers 12a to 12e. rectifying sections 14a to 14e are arranged in spaces 13a to 13e, respectively.

Rectifying sections 14b to 14e are arranged in spaces 13b to 13e. The rectifying section 14a may or may not be arranged in the space 13a. For facilitating stabilization of a dispersed state of the gas introduced in the honeycomb catalyst layer 12a, it is preferable to have the rectifying section 14a.

For example, honeycomb catalyst layers may be arranged in such manner as that: honeycomb catalyst layers 12a and 12b are arranged together and combined to give a set of catalyst layers (without the space 13b); honeycomb catalyst layers 12c, 12d, and 12e are arranged together and combined to give a set of catalyst layers (without the space 13d or 13e); a space is provided only between these sets; and a rectifying section is arranged in the space, and a rectifying section may be arranged in a space below the set of honeycomb catalyst layers 12a and 12b.

In the case of arranging ten, twenty, or more honeycomb catalyst layers, two, three, four or more catalyst layers can be combined into a set, and a rectifying sections can be installed in spaces between sets and in a space below the lowest set.

The honeycomb catalyst layer, the space, and the rectifying section will be described below.

[Honeycomb Catalyst Layer]

Honeycomb catalyst layers 12a to 12e are made of honeycomb catalyst. The honeycomb catalyst is formed by immobilizing a catalyst on the surface of a support such as a bundle of tubes with an inner diameter of a few millimeters to tens millimeters or a honeycomb structure having a cell density of several tens to hundreds cells per square inch.

The honeycomb catalyst has many cells (narrow tubular channels) formed parallel to each other. The cell can have any shape (cross-section shape in cross direction), including general triangle, rectangle, hexagon, and a shape formed by stacking flat and corrugated plates (as shown in FIG. 3 of JP-A 2009-262145 and FIG. 6 of JP-A 2008-110341, in which a cell has an approximate triangular shape with a rounded corner and two curvilinear sides).

Each cell preferably has a cross-section area in cross direction of 0.01 to 100 $cm^2$, more preferably 0.03 to 50 $cm^2$, and even more preferably 0.05 to 10 $cm^2$. For facilitating passing of a liquid and a gaseous reactants, the cross-section area is preferably not less than 0.01 $cm^2$, more preferably not less than 0.03 $cm^2$, and even more preferably not less than 0.05 $cm^2$. For increasing a contact efficiency of a reactant with the honeycomb catalyst, the cross-section area is preferably not more than 100 $cm^2$, more preferably not more than 50 $cm^2$, and even more preferably not more than 10 $cm^2$.

The honeycomb catalyst can be produced by any method. In a honeycomb structure support, a catalyst is preferably immobilized on an inner wall to form a thin catalyst film having a thickness of 0.01 to 500 μm, more preferably 0.1 to 100 μm, even more preferably 1 to 50 μm, and even more preferably 5 to 50 μm.

Migration of a reactant and a product in a catalyst film is under diffusion control. A thin catalyst film having a thickness of not more than 500 μm can facilitate mass transfer between the inside and the outside of the catalyst film, make an effective use all the way of the inside of the catalyst film, and further suppress overreactions of an intermediate in the catalyst film. For suppressing side reactions to increase a selectivity of the reaction, the thickness is preferably not more than 100 μm, and more preferably not more than 50 μm. For ensuring catalyst film strength and durability of the strength, the thickness is preferably not less than 0.01 μm, more preferably not less than 0.1 μm, even more preferably not less than 1 μm, and even more preferably not less than 5 μm.

The catalyst can be immobilized in a thin film state on the honeycomb structure support by any known method, for example, by physical vapor-deposition such as sputtering, chemical vapor-deposition, solution impregnation, and various coating methods with a binder, such as blade coating, spraying, dipping, spin coating, gravure coating, and dye coating.

Figure 3:
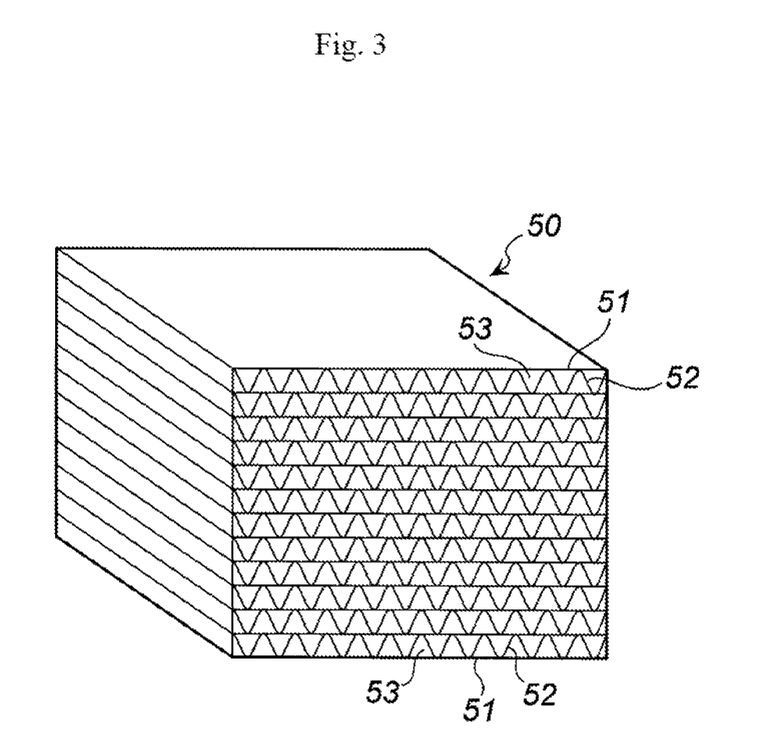
FIG. 3 shows a perspective view of an example of the honeycomb catalyst layer used in the method of the present invention.

Any support can be used if it can form a honeycomb structure in the column reactor. The support may be formed in advance in a honeycomb structure, or be a honeycomb structure constructed with flat plates 51 and corrugated plates 52 that are layered to form cells 53 as shown in FIG. 3.

Any material commonly used for honeycomb structures can be used, including inorganic materials such as metal foils and ceramics. For increasing uniformity in thickness of a thin catalyst film, a flat support is preferably processed to immobilize a catalyst thereon and then shaped into a honeycomb structure. Metal foils are preferably used due to good processability.

Any known active material can be used to compose the honeycomb catalyst. In general, preferably used are one or more metals selected from Groups 5, 6, 7, 8, 9, 10, 11, and 12 elements of the periodic table.

Examples of the active material include single Cu of Group 11 and combinations of Cu and one or more metal elements such as Nb of Group 5, Cr and Mo of Group 6, Mn of Group 7, Fe and Ru of Group 8, Co and Rh of Group 9, Ni, Pd, and Pt of Group 10, and Zn of Group 12. Active materials containing Cu and Ni are preferably used. Such an active material may be further fixed on a support such as silica, alumina, titania, zeolite, silica-alumina, zirconia, and diatomaceous earth to be used.

In case of using an active material containing a Group 11 element and other element(s) to compose the honeycomb catalyst of the present invention, for efficiently producing a tertiary amine, a mass ratio of the Group 11 element to a total of the other element(s), Group 11 element/other element(s), is preferably 0.1/1 to 100/1, more preferably 1/1 to 50/1, and even more preferably 3/1 to 30/1.

The honeycomb catalyst may further contain a binder that does not act as an active material by itself but fixes an active material to form a thin catalyst film.

The binder is a polymer or an inorganic compound having properties for binding an active material with each other or with the surface of a support, and chemical-resistant and heat-resistant properties for enduring reaction conditions, while having no adverse effect on a reaction system.

Examples of the binder include cellulose resins such as carboxymethyl cellulose and hydroxyethyl cellulose; fluorinated resins such as polytetrafluoroethylene and poly(vinylidene fluoride); polymer compounds such as urethane resins, epoxy resins, polyester resins, phenol resins, melamine resins, silicone resins, polyvinyl alcohols, polyimide resins, and polyamide-imide resins; and inorganic sols such as silica, alumina, titania, silica-alumina, and zirconia.

In production of the honeycomb catalyst, the content of the binder to the active material is preferably 10 to 80 parts by mass, more preferably 15 to 60 parts by mass, and even more preferably 20 to 30 parts by mass to 100 parts by mass of active material. From the viewpoint of binding with the surface of a support, the content is preferably not less than 10 parts by mass, more preferably not less than 15 parts by mass, and even more preferably not less than 20 parts by mass to 100 parts by mass of active material. From the viewpoint of activity of the active material, the content is preferably not more than 80 parts by mass, more preferably not more than 60 parts by mass, and even more preferably not more than 30 parts by mass to 100 parts by mass of active material.

The inner structure of the honeycomb catalyst may be a continuous compact phase or a porous texture, depending largely on a kind of the active material composing a catalyst film, a method of forming the catalyst film, and the like.

For example, a thin film formed on the surface of a support by sputtering or chemical vapor-deposition or the like has a continuous compact phase. A thin film formed on the surface of a support by a wet or dry coating of a powdered active material has a porous texture.

A honeycomb catalyst layer can be constructed in the column reactor by those methods including:

(I) processing layered flat and corrugated films of catalyst to form a honeycomb catalyst in a tube or strip shape (which may be further inserted in an appropriate container such as a cylinder) and loading the formed catalyst in the column reactor; and (II) packing a honeycomb catalyst shaped in advance to fit in the column reactor (which catalyst may be further inserted in an appropriate container such as a cylinder) in the column reactor.

For preventing a widening distribution of residence time of a reaction fluid in a honeycomb catalyst layer, the honeycomb catalyst layer preferably has a narrow tubular channel parallel to a flow direction of the reaction fluid.

In case of using a column reactor of shell-and-tube heat exchanger type, a temperature of a reaction part can be controlled by loading a honeycomb catalyst in a tube and flowing a heat medium in a shell without a honeycomb catalyst.

In some cases, a reaction can be continuously conduced in a reactor 1 of column type or shell-and-tube heat exchanger type, combined with a buffer tank 3 as shown in FIG. 1. In this system, a liquid raw material is circulated via a circulation pump 35 and a gaseous material is continuously supplied to the reactor 1. A reacted gas is separated from the reaction in the buffer tank 3.

[Space and Rectifying Section]

In the column reactor 1, spaces 13a to 13e are provided below the lowest honeycomb catalyst layer 12a and between each of honeycomb catalyst layers 12a to 12e. Rectifying sections arranged in the spaces can prevent partial or whole back-mixing of liquid and gas between the upper and the lower neighboring honeycomb catalyst layers to bring a flow to a plug flow in the column reactor, which is generally a completely mixed flow. Therefore, a honeycomb catalyst layer, a space, and a rectifying section are preferably set to a construction unit and several units are preferably installed in the column reactor.

Rectifying sections 14a to 14e are arranged in spaces 13a to 13e without contacting with either the upper or lower adjacent honeycomb catalyst layer.

Each distance between the rectifying sections 14a to 14e and the adjacent honeycomb catalyst layers 12a to 12e is preferably 0.5 to 999 mm, more preferably 1 to 499 mm, and even more preferably 2 to 199 mm. For preventing back mixing of liquid and gas between the upper and the lower neighboring honeycomb catalyst layers, the distance is preferably not less than 0.5 mm, more preferably not less than 1 mm, and even more preferably not less than 2 mm. For increasing a packing efficiency of the catalyst layers in the reactor, the distance is preferably not more than 999 mm, more preferably not more than 499 mm, and even more preferably not more than 199 mm.

For preventing back mixing of liquid and gas between the upper and the lower neighboring honeycomb catalyst layers, each upper distance between the rectifying sections 14a to 14e and the upper adjacent honeycomb catalyst layers 12a to 12e and each lower distance between the rectifying sections 14a to 14e and the lower adjacent honeycomb catalyst layers 12a to 12e are preferably at a ratio, upper distance/lower distance, of 1/1000 to 1000/1, more preferably 1/100 to 100/1, even more preferably 1/10 to 10/1, and even more preferably 1/1.

The rectifying section 14a is more preferably arranged in a space below the lowest honeycomb catalyst layer 12a to suppress back mixing from the lowest layer 12a to the space 13a. The same applies to a space above the top honeycomb catalyst layer 12e. A rectifying section is more preferably arranged in the space to suppress back mixing from the space to the top layer 12e.

Each of spaces 13a to 13e preferably has a length of 5 to 1000 mm, more preferably 10 to 500 mm, and even more preferably 20 to 200 mm. For preventing back mixing of liquid and gas between the upper and the lower neighboring honeycomb catalyst layers, the length is preferably not less than 5 mm, more preferably not less than 10 mm, and even more preferably not less than 20 mm. For increasing a packing efficiency of the catalyst layers in the reactor, the length is preferably not more than 1000 mm, more preferably not more than 500 mm, and even more preferably not more than 200 mm. The upper limit is determined by considering a size of the column reactor 1 and the number of honeycomb catalyst layers packed therein. In the present invention, a distance between spaces 13a to 13e is defined by spaces formed after rectifying sections are arranged (a space excluding a rectifying section).

In case of installing three or more catalyst layers, the reactor has several spaces, which may have the same or different lengths.

Each of rectifying sections 14a to 14e arranged in spaces 13a to 13e produces an effect to prevent a part or whole of gas and liquid from flowing from a downstream space (near to the top of the column reactor 1) contacting with the upper honeycomb catalyst layer to an upstream space (near to the bottom of the column reactor 1) contacting with the lower honeycomb catalyst layer (effect to prevent a back flow).

A rectifying section can be used if it has a small pressure loss to the flowing of gas or liquid. The rectifying section preferably has several penetrating passages (holes), allows gas and liquid passing through the part, and suppresses a horizontal flow between passages close to each other. In the rectifying section having several penetrating passages, a bubble acts like a plug in a passage during passing the passage upwardly to prevent liquid from flowing backward in the passage from top down. Specific examples of the means preferably used include honeycomb structures having vertical passages in shapes of triangle, rectangle, hexagon, and the like, defined by porous and thin plates, and structures constructed with two mesh sheets and a structured packing such as a spherical or cylindrical regular packing sandwiched between sheets. More preferred is a perforated plate that is easily processed and has round passages with the same size.

Two or more rectifying sections may be arranged in a space, and may or may not be contacted with each other, provided that these rectifying sections each have several penetrating passages (holes). Two or more rectifying sections may be of the same or different kind The rectifying section desirably has a passage caliber equal to or smaller than the maximum size of a bubble in the column reactor 1, and preferably not more than 8 mm, more preferably not more than 7 mm, and even more preferably not more than 6 mm. For reducing an amount of unreacted reactant in the column reactor 1 at the end of the reaction, the caliber is preferably not less than 0.5 mm, more preferably not less than 2 mm, and even preferably not less than 3 mm.

The passage caliber of the rectifying section is preferably 0.5 to 8 mm, more preferably 2 to 7 mm, and even more preferably 3 to 6 mm.

The rectifying section may be a perforated plate or a thick honeycomb plate. The rectifying section may have any aperture ratio from 1 to about 100% according to a kind of the part.

In case of using a perforated plate as the rectifying section, an aperture ratio to the area of the perforated plate is related to the passage caliber of the perforated plate. For effective prevention of back mixing, the aperture ratio is preferably not more than 70%, more preferably not more than 60%, even more preferably not more than 50%, and even more preferably not more than 45%. For reducing a pressure loss of gas and liquid during passing through the perforated plate and preventing generation of a stagnant part in the contacting column 1, the aperture ratio to the area of the perforated plate is preferably not less than 1%, more preferably not less than 10%, even more preferably not less than 20%, and even more preferably not less than 31%.

More specifically, the aperture ratio to the area of the perforated plate is preferably 1 to 70%, more preferably 10 to 60%, even more preferably 20 to 50%, and even more preferably 31 to 45%.

In case of using a perforated plate as the rectifying section, for suppressing distortion of the plate against flowing gas and liquid, the perforated plate preferably has a thickness of not less than 0.5 mm, more preferably not less than 0.8 mm, and even more preferably not less than 1 mm. For suppressing a pressure loss, ensuring workability, and suppressing an increase in mass, the thickness is preferably not more than 20 mm, more preferably not more than 10 mm, and even more preferably not more than 5 mm.

In case of using a perforated plate as the rectifying section, more specifically, the thickness of the perforated plate is preferably 0.5 to 20 mm, more preferably 0.8 to 10 mm, and even more preferably 1 to 5 mm.

In case of using a thick honeycomb plate as the rectifying section, an aperture ratio to the area of the thick honeycomb plate may sometimes reach to about 100%. In this case, a key factor for preventing back mixing of liquid is a passage caliber of the rectifying section. The aperture ratio may be high. There are various thick honeycomb plates produced by various methods, providing a high degree of freedom in selection of a size of the perforate and a size of the pitch. A thick honeycomb plate having a low aperture ratio thus can also be selected. In this case, for reducing a pressure loss of gas and liquid during passing through the thick honeycomb plate and suppressing generation of a stagnant part in the contacting column 10, the aperture ratio is preferably not less than 1%, more preferably not less than 10%, even more preferably not less than 20%, and even more preferably not less than 31%.

In case of using a thick honeycomb plate as the rectifying section, rigidity of the thick honeycomb plate depends on a thickness of the plate. From the viewpoint of rigidity, the thickness is preferably not less than 5 mm, more preferably not less than 10 mm, and even more preferably not less than 20 mm. For effective use of the space in the column reactor 1, the thickness is preferably not more than 25% of the height of a honeycomb structure.

<Material-Supplying Means>

A liquid alcohol and a gaseous primary or secondary amine can be separately supplied to the column reactor 1 shown in FIGS. 1 and 2, as shown in FIG. 1, or preferably introduced in the same space, passed through an alleyway or a narrow path, and then supplied to the column reactor 1, as shown in FIG. 2.

In FIG. 1, the column reactor 1 receives a gaseous material supply from a gas feeder 2 installed at the bottom in the column and a separate liquid supply from a line 25.

In FIG. 2, raw materials are supplied to the column reactor 1 through an alleyway. The alleyway can be provided by forming it in the bottom part itself of the column reactor 1 or by combining a supply line 23 of a liquid alcohol and a supply line 25 of a gaseous primary or secondary amine to form one line and forming the alleyway in this line.

An embodiment in FIG. 2 illustrates a method of supplying raw materials through a supply nozzle 2A (see, FIG. 4) installed at the bottom outside the column reactor 1. It is noted that the supply nozzle 2A may be arranged inside the column reactor 1, although it is arranged outside the column reactor 1 in FIG. 2.

The column reactor 1 in FIG. 1 can also include a supply nozzle 2A as shown in the column reactor 1 in FIG. 2 instead of the gas feeder 2 installed at the bottom in the column. In this case, the supply nozzle 2A can be arranged at the bottom either inside or outside the column reactor 1.

In case of using a supply nozzle 2A shown in FIG. 4(a), a gaseous primary or secondary amine from the line 23 and a liquid alcohol from the line 25 are introduced in the same space 2a of the supply nozzle 2A to give a mixed phase.

The mixed phase passes through an alleyway 2b and spreads as a spray in the column container 1 having a wider inner diameter than the alleyway 2b. In a spray flow of the mixed phase, bubbles are dispersed to give a mixed state of large and small bubbles.

In case of using a supply nozzle 2A shown in FIG. 4(b), a gaseous primary or secondary amine from the line 23 and a liquid alcohol from the line 25 are introduced in the same space 2a of the supply nozzle 2 to form a mixed phase.

The mixed phase passes through an alleyway 2b and spreads as a spray in the column container 1 having a wider inner diameter than the alleyway 2b.

By installing an impingement plate (jet-preventing plate) 2d with an interval in the direction facing to an exit of the alleyway 2b, the mixed phase collides against the impingement plate 2d to disperse bubbles more intensely and form a more mixed state of large and small bubbles than by using the supply nozzle 2A shown in FIG. 4(a).

The impingement plate 2d preferably has an equal or larger diameter than a diameter (d1) of the alleyway 2b, and is preferably adjusted to increase the diameter with increasing distance from the exit of the nozzle. The impingement plate 2d may have the same diameter as the inner diameter of the column reactor 1. In this case, the impingement plate 2d may be a perforated plate having a through-hole for facilitating gas and liquid flowing. For example, a ratio of a distance (H) of the impingement plate 2d from the exit of the nozzle to a diameter (d1) of the alleyway 2b, H/d1, is preferably not more than 100, more preferably not more than 20, even more preferably not more than 10, and even more preferably not more than 5.

For example, the impingement plate 2d is of a cup shape in which the bottom surface serves as the impingement plate 2d and a peripheral sidewall has a structure allowing the mixed phase to flow through the sidewall.

In case of using a supply nozzle 2A shown in FIG. 4(c), a gaseous primary or secondary amine from the line 23 and a liquid alcohol form the line 25 are introduced in the same space (first space 2a) of the supply nozzle 2A to form a mixed phase.

The mixed phase passes through an alleyway 2b to reach a second space 2c having a wider inner diameter than the alleyway 2b, and spreads as a spray in the column container 1 having a wider inner diameter than the second space 2c. This construction disperses bubbles more intensely in the mixed phase flow and gives a more mixed state of large and small bubbles than by using the supply nozzle 2A shown in FIG. 4(a).

The first space 2a has a tapering inner wall and a decreasing inner diameter toward the alleyway 2b, and the second space 2c has a tapering inner wall and an increasing inner diameter from the alleyway 2b toward the exit of the nozzle (Venturi shape).

The inner diameters of the first and second spaces 2a and 2c are the same as each other in FIG. 4(c), but either inner diameter may be larger than the other.

For enhancing the dispersion of bubbles in a mixed phase flow of an alcohol and a gaseous primary or secondary amine, in the supply nozzle 2A shown in FIGS. 4(a) to 4(c), a ratio of the inner diameter (d1) of the alleyway 2b to the maximum diameter (d2) of a supply route of the mixed phase leading to the alleyway 2b, d1/d2, is preferably within the range of 0.01 to 0.9, more preferably 0.01 to 0.3, and even more preferably 0.03 to 0.3.

The maximum diameter (d2) is an inner diameter of the space 2a in FIGS. 4(a) and 4(b), or a maximum diameter of the first space 2a in FIG. 4(c).

The column reactor 1 receiving a supply of gas and liquid raw materials from the supply nozzle 2A preferably has an inner diameter 3 to 500 times, more preferably 70 to 400 times, and even more preferably 130 to 300 times as large as the inner diameter of the alleyway 2b in the supply nozzle 2A shown in FIGS. 4(a) to 4(c).

The supply nozzle 2A shown in FIGS. 4(a) and 4(b) preferably has a ratio of a length L to an inner diameter d2, L/d2, of 1 to 5, and more preferably 1.2 to 2. From the viewpoint where an appropriate pressure loss facilitates gas dispersion, the ratio is preferably not less than 1, and more preferably not less than 1.2. For preventing an excess pressure loss, the ratio is preferably not more than 5, and more preferably not more than 2.

The supply nozzle 2A shown in FIG. 4(c) has a Venturi shape as described above, and the ratio, L/d2, may be less than 1.

As described above, a supply route of liquid and gaseous raw materials, that narrow and then expands, can disperse bubbles in a gas-liquid mixed phase flow to form a mixed state of large and small bubbles. This promotes the gas to be dissolved in the liquid and enables the whole catalyst cells to be used effectively when the mixed phase flow passes through the honeycomb catalyst layer.

<Method for Producing a Tertiary Amine with the Column Reactor>

The method for producing a tertiary amine of the present invention uses the column reactor shown in FIG. 1 or 2 as described above in a part or the whole process of production of the tertiary amine.

In the production of a tertiary amine with the column reactor 1 shown in FIG. 1 or 2, the tertiary amine is generated through a sequence of reactions of:

(i) dehydrogenation of an alcohol to produce an aldehyde;
(ii) addition reaction of a raw material amine to the aldehyde and dehydration; and
(iii) hydrogen reduction of an imine and/or enamine generated by addition reaction and dehydration to produce a tertiary amine. The reaction (ii) can progress without a catalyst used in the reaction (i) or (iii).

These reactions (i) to (iii) can be conducted in the same reactor or separately in different reactors.

Alternatively, the reaction (i) is conducted in a reactor and the reaction (ii) is conducted in other reactor separating from the reaction (i) or (iii), and the product from the reaction (ii) can be added to a reaction system in the reactor conducting the reaction (i) to simultaneously conducting reactions (i) and (iii).

In case of conducting the reaction (ii) in the other reactor than the column reactor 1 shown in FIG. 1 or 2, a primary or secondary amine may not be supplied to the column reactor 1.

In the present invention, conditions in the reaction between an alcohol and a primary or secondary amine also depend on kinds of a reactant, a product, and a catalyst.

With reference to FIGS. 1 and 2, the method for producing a tertiary amine of the present invention will be described. The method of the present invention uses the column reactor 1 in an upflow mode that can prevent a part not wetted with a liquid material, or what so called dry spots, from occurring, by sufficiently supplying a liquid material throughout honeycomb catalyst layers 12a to 12e packed in the column reactor 1.

To the column reactor, a primary or secondary amine can be supplied in a gaseous state or in a partially or fully dissolved state in a liquid material.

A gaseous primary or secondary amine can be supplied in the form of a mixture with hydrogen, nitrogen, and/or a rare gas, or separately from a supply of hydrogen, nitrogen, and/or a rare gas. For maintaining an activity of a catalyst, the primary or secondary amine is preferably supplied together with hydrogen, nitrogen, and/or a rare gas in a mixed form.

A gas material can be supplied to the column reactor through a method, for example, of blowing the gas material into a liquid material from a single tube, of blowing the gas material from a multi-tube nozzle or a linear or curve porous nozzle, of introducing the gas material in a static mixer together with a liquid material, or of simultaneously supplying the gas and a liquid materials to a nozzle having a narrow passage arranged at the bottom of the column reactor (using the column reactor including the supply nozzle 2A shown in FIG. 2). Among these methods, preferred is the method of simultaneously supplying a gas and a liquid materials to a nozzle having a narrow passage, because this method achieves high gas-liquid mass transfer under conditions of a relatively large gas flow, and promises a synergistic effect.

A primary or secondary amine in a partially or fully dissolved state in a liquid material can be supplied to the column reactor, for example, through a method of agitating bubbles by supplying the gaseous or liquid primary or secondary amine to a mixing tank containing a liquid material or a general dissolving method using a common dissolving means such as a bubble column, a trayed column, a packed column, a wet wall, or a spray column.

In the start of the reaction, a buffer tank 3 contains a raw material alcohol. The alcohol in the buffer tank 3 is supplied to the column reactor 1 at the bottom thereof through the line 25 by activating an outer circulation pump 35 with a valve (e.g., electromagnetic valve) 33 opened.

A primary and/or secondary amine in a storage tank 5 is supplied through a line 21 with a valve (e.g., electromagnetic valve) 31 opened. At the same time, hydrogen (and nitrogen or rare gas) in a storage tank 6 is supplied through a line 22 with a valve (e.g., electromagnetic valve) 32 opened. The primary and/or secondary amine and the hydrogen gas are combined in a line 23 to form a gaseous mixture and supplied to the column reactor 1.

In case of using the column reactor 1 shown in FIG. 1, the gaseous mixture is supplied through a gas feeder 2 at the bottom of the column.

In case of using the column reactor 1 attached with the supply nozzle 2A shown in FIG. 2 or the column reactor 1 shown in FIG. 1 attached with the supply nozzle 2A, the gaseous primary or secondary amine and the liquid alcohol are introduced in the same space in the supply nozzle 2A and mixed therein to form a mixed phase, that mixed phase passes through an alleyway to be sprayed into the column reactor.

Figure 4:
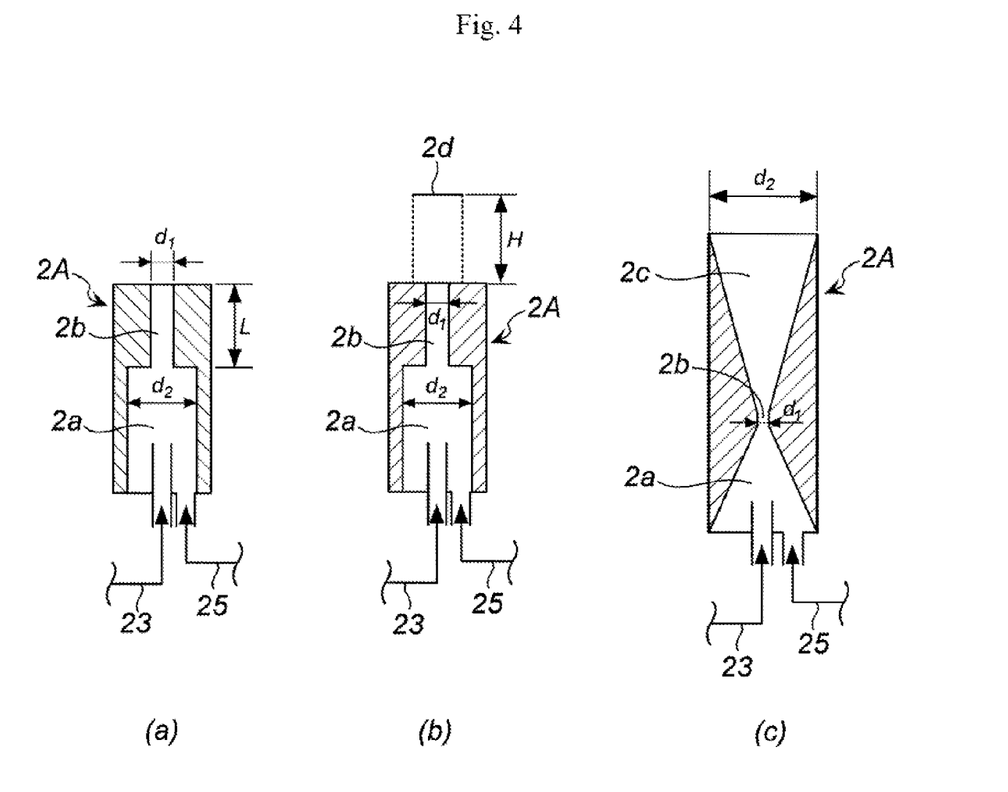
FIG. 4(a) shows a vertical sectional view of a supply nozzle provided in the production equipment in FIG. 2.
FIG. 4(b) shows a vertical sectional view of a supply nozzle provided in the production equipment in FIG. 2.
FIG. 4(c) shows a vertical sectional view of a supply nozzle provided in the production equipment in FIG. 2.

In the method of the present invention, a superficial gas velocity of a gaseous and a liquid materials at the alleyway 2b in the supply nozzle 2A shown in FIGS. 4(*a*) to 4(*c*) is preferably 0.01 to 250 Nm/s, more preferably 2 to 100 Nm/s, and even more preferably 3 to 50 Nm/s. The higher the superficial gas velocity is, the higher proportion of fine bubbles is in bubbles. Thus, the superficial gas velocity is preferably not less than 0.01 Nm/s, more preferably not less than 2 Nm/s, and even more preferably not less than 3 Nm/s, calculated based on the standard state volume.

For stabilizing gas introduction to a honeycomb catalyst in the column reactor, the superficial gas velocity is preferably not more than 250 Nm/s, more preferably not more than 100 Nm/s, and even more preferably not more than 50 Nm/s.

In the method of the present invention, a supply pressure of a mixed phase of a liquid alcohol and a gaseous primary or secondary amine to the column reactor 1 attached with the supply nozzle 2A shown in FIGS. 4(*a*) to 4(*c*) is preferably 0.005 to 0.9 MPa, more preferably 0.01 to 0.2 MPa, and even more preferably 0.02 to 0.1 MPa in gauge pressure. For achieving a sufficient effect to disperse bubbles, the supply pressure is preferably not less than 0.005 MPa, more preferably not less than 0.01 MPa, and even more preferably not less than 0.02 MPa in gauge pressure. For suppressing condensation of a gaseous material, the supply pressure is preferably not more than 0.9 MPa, more preferably not more than 0.2 MPa, and even more preferably not more than 0.1 MPa.

The raw material alcohol is preferably a linear or branched, saturated or unsaturated, aliphatic alcohol having 6 to 36 carbon atoms, more preferably having 8 to 22 carbon atoms, even more preferably having 10 to 18 carbon atoms, and even more preferably having 12 to 14 carbon atoms. Examples of the alcohol include hexyl alcohol, octyl alcohol, decyl alcohol, lauryl alcohol, myristyl alcohol, palmityl alcohol, stearyl alcohol, behenyl alcohol, oleyl alcohol etc. and mixed alcohols thereof, as well as Ziegler alcohols produced by the Ziegler method, oxo alcohols produced by the oxo method, and Guerbet alcohols.

The raw material primary or secondary amine is preferably an aliphatic primary or secondary amine, more preferably having 1 to 24 carbon atoms, more preferably having 1 to 12 carbon atoms, more preferably having 1 to 4 carbon atoms, and even more preferably 1 to 2 carbon atoms. Examples of the aliphatic primary or secondary amine include methylamine, dimethylamine, ethylamine, diethylamine, dodecylamine, and didodecylamine.

The primary and/or secondary amine, hydrogen gas, and the alcohol supplied to the column reactor 1 from the bottom react through the course of passing sequentially honeycomb catalyst layers 12a to 12e (the continuous phase is liquid).

During the course, rectifying sections 14a to 14e arranged in spaces 13a to 13e prevent a back flow of gas or liquid to increase a reaction efficiency. The reaction in the column reactor 1 is preferably kept under temperature control with a jacket or a heat-exchange pipe arranged in the column.

A reaction product and an unreacted alcohol in the column reactor 1 are transferred through a line 24 to the buffer tank 3 containing a raw material alcohol. In this stage, the buffer tank 3 contains a mixture of the alcohol and the reaction product.

Then, the same procedures are repeated to supply a primary and/or secondary amine in the storage tank 5, hydrogen gas (and nitrogen or rare gas) in the storage tank 6 and a content (mixture) in the buffer tank 3 to the column reactor 1 at the bottom thereof to react these materials. These procedures are cycled to continue the reaction.

It is noted that the primary and/or secondary amine can be supplied not to the column reactor 1, but to the buffer tank 3 to conduct the reaction (ii) separately in the buffer tank 3 from the reactions (i) and (iii) progressing in the column reactor 1.

An unreacted gaseous primary or secondary amine and moisture in the buffer tank 3 are continuously discharged through a conduit 26a and a line 27 with a valve (e.g., electromagnetic valve) 34 opened.

In components passing the conduit 26a, vapor or mist of an alcohol and/or a produced tertiary amine can be contained in addition to the above. The vapor or mist is condensed in a packed column 4 and returned through a line 26b to the buffer tank 3.

In the method of the present invention, a supply rate G (Nm$^3$/Hr) of a gaseous reactant, calculated based on the standard state volume, varies and preferably the gas supply rate is controlled depending on an activity of a catalyst packed in the column reactor 1.

A ratio of the gas supply rate G to a supply rate L (m$^3$/Hr) of a liquid alcohol or a mixture of an alcohol and a reaction product, G/L, is preferably 0.1 to 50, more preferably 0.3 to 30, and even more preferably 1 to 20. From the viewpoint of residence time of a gaseous reactant, G/L is preferably not less than 0.1, more preferably not less than 0.3, and even more preferably not less than 1. For reducing a discharge of unreacted gas, G/L is preferably not more than 50, more preferably not more than 30, and even more preferably not more than 20.

In the method of the present invention, a pressure at a catalytic reaction field is preferably 0.013 to 0.3 MPa, more preferably 0.04 to 0.25 MPa, and even more preferably 0.1 to 0.2 MPa in absolute pressure. A low pressure at a catalytic reaction site facilitates discharge of moisture generated along with the reaction from the reaction system to promote the progress of the reaction and hold an activity of the catalyst. The reaction under a lower pressure than ordinary pressure gives a burden in facilities, such as vacuum fixture.

A reaction temperature, which may vary according to a kind of the catalyst, is preferably 150 to 300° C., and more preferably 160 to 250° C. At a reaction temperature within the proper range, the reaction progresses at a controlled rate and a side reaction can be prevented.

In the method of the present invention, a pressure difference between pressure at an entrance and an exit of the column reactor 1 is preferably not more than 0.2 MPa in gauge pressure. At a pressure loss within this range, a side reaction is suppressed to obtain a better yield, and a gaseous primary or secondary amine hardly turns into liquid, and a heating control can be easier.

For efficiently producing a tertiary amine, the method of the present invention preferably continues the reaction until an amount of an unreacted alcohol in a reaction mixture reaches to 0 to 5% by mass, more preferably 0.1 to 3% by mass, and even more preferably 0.5 to 2% by mass.

According to the method of the present invention, a gaseous primary or secondary amine can be efficiently reacted with a liquid alcohol to produce an intended tertiary amine at high yield.

The tertiary amine produced from the alcohol and the primary or secondary amine by the method of the present invention has an alkyl and/or alkenyl group derived from the alcohol and a nitrogen atom derived from the primary or secondary amine, in which a hydrogen atom bonding to the nitrogen atom is substituted with the alkyl and/or alkenyl group. For example, dodecyl alcohol and dimethylamine produce a corresponding tertiary amine, N-dodecyl-N,N-dimethylamine, which is distinguished from by-product tertiary amines, N,N-didodecyl-N-methylamine and N,N,N-tridodecylamine, from methylamine and ammonia generated from disproportionation of dimethylamine.

The present invention further discloses the following methods relating to the embodiments described above:

<1> a method for producing a tertiary amine, using a column reactor packed with catalyst layers, containing supplying liquid and gaseous raw materials from the bottom of the column, reacting the raw materials in the column, and discharging a product from the top of the column,
wherein the column reactor includes two or more honeycomb catalyst layers as the catalyst layers, spaces between said two or more honeycomb catalyst layers, and a rectifying section as means for preventing a partial or whole back flow of the raw materials, arranged in the space without contacting with the honeycomb catalyst layer;

<2> the method for producing a tertiary amine according to <1>, wherein the raw materials are a liquid alcohol and a gaseous primary or secondary amine;

<3> the method for producing a tertiary amine according to <1> or <2>, wherein the alcohol is preferably a linear or branched, saturate or unsaturated aliphatic alcohol having 6 to 36 carbon atoms, more preferably having 8 to 22 carbon atoms, even more preferably having 10 to 18 carbon atoms, and even more preferably having 12 to 14 carbon atoms, such as hexyl alcohol, octyl alcohol, decyl alcohol, lauryl alcohol, myristyl alcohol, palmityl alcohol, stearyl alcohol, behenyl alcohol or oleyl alcohol, or mixed alcohols thereof, or a Ziegler alcohol produced by the Ziegler method, an oxo alcohol produced by the oxo method, or a Guerbet alcohol;

<4> the method for producing a tertiary amine according to any one of <1> to <3>, wherein the primary or secondary amine is preferably an aliphatic primary or secondary amine such as methylamine, dimethylamine, ethylamine, or diethylamine;

<5> the method for producing a tertiary amine according to any one of <1> to <4>, wherein the space in the column reactor preferably has a length of 5 to 1000 mm, more preferably 10 to 500 mm, and even more preferably 20 to 200 mm;

<6> the method for producing a tertiary amine according to any one of <1> to <4>, wherein the space in the column reactor preferably has a length of not less than 5 mm, more preferably not less than 10 mm, and even more preferably not less than 20 mm;

<7> the method for producing a tertiary amine according to any one of <1> to <4>, wherein the space in the column reactor preferably has a length of not more than 1000 mm, more preferably not more than 500 mm, and even more preferably not more than 200 mm;

<8> the method for producing a tertiary amine according to any one of <1> to <7>, wherein the number of honeycomb catalyst layers in the column reactor is preferably not less than 3, and more preferably not less than 4;

<9> the method for producing a tertiary amine according to any one of <1> to <8>, wherein a perforated plate has preferably a thickness of 0.5 to 20 mm, more preferably 0.8 to 10 mm, even more preferably 1 to 5 mm as the rectifying section of the column reactor;

<10> the method for producing a tertiary amine according to any one of <1> to <8>, wherein a perforated plate has preferably a thickness of not less than 0.5 mm, more preferably not less than 0.8 mm, and even more preferably not less than 1 mm as the rectifying section of the column reactor;

<11> the method for producing a tertiary amine according to any one of <1> to <8>, wherein a perforated plate has preferably a thickness of not more than 20 mm, more preferably not more than 10 mm, and even more preferably not more than 5 mm as the rectifying section of the column reactor;

<12> the method for producing a tertiary amine according to any one of <1> to <11>, wherein the rectifying section in the column reactor preferably has a passage caliber of 0.5 to 8 mm, more preferably 2 to 7 mm, and even more preferably 3 to 6 mm;

<13> the method for producing a tertiary amine according to any one of <1> to <11>, wherein the rectifying section in the column reactor preferably has a passage caliber of not less than 0.5 mm, more preferably not less than 2 mm, and even more preferably not less than 3 mm;

<14> the method for producing a tertiary amine according to any one of <1> to <11>, wherein the rectifying section in the column reactor preferably has a passage caliber of not more than 8 mm, more preferably not more than 7 mm, and even more preferably not more than 6 mm;

<15> the method for producing a tertiary amine according to any one of <1> to <14>, wherein the rectifying section in the column reactor preferably has an aperture ratio of 1 to 70%, more preferably 10 to 60%, even more preferably 20 to 50%, and even more preferably 31 to 45%;

<16> the method for producing a tertiary amine according to any one of <1> to <14>, wherein the rectifying section in the column reactor preferably has an aperture ratio of not less than 1%, more preferably not less than 10%, even more preferably not less than 20%, and even more preferably not less than 31%;

<17> the method for producing a tertiary amine according to any one of <1> to <14>, wherein the rectifying section in the column reactor preferably has an aperture ratio of not more than 70%, more preferably not more than 60%, even more preferably not more than 50%, and even more preferably not more than 45%;

<18> the method for producing a tertiary amine according to any one of <1> to <17>, wherein a pressure at a catalytic reaction field in the column reactor is preferably 0.013 to 0.3 MPa, more preferably 0.04 to 0.25 MPa, and even more preferably 0.1 to 0.2 MPa in absolute pressure;

<19> the method for producing a tertiary amine according to any one of <1> to <17>, wherein a pressure at a catalytic reaction field in the column reactor is preferably not less than 0.013 MPa, more preferably not less than 0.04 MPa, even more preferably not less than 0.1 MPa in absolute pressure;

<20> the method for producing a tertiary amine according to any one of <1> to <17>, wherein a pressure at a catalytic reaction field in the column reactor is preferably not more than 0.3 MPa, more preferably not more than 0.25 MPa, even more preferably not more than 0.2 MPa in absolute pressure;

<21> the method for producing a tertiary amine according to any one of <1> to <20>, wherein a reaction temperature at a catalytic reaction field in the column reactor is preferably 150 to 300° C., and more preferably 160 to 250° C.;

<22> the method for producing a tertiary amine according to any one of <1> to <21>, wherein a distance between a rectifying section and the adjacent honeycomb catalyst layer in the column reactor is preferably 0.5 to 999 mm, more preferably 1 to 499 mm, and even more preferably 2 to 199 mm;

<23> the method for producing a tertiary amine according to any one of <1> to <21>, wherein a distance between a rectifying section and the adjacent honeycomb catalyst layer in the column reactor is preferably not less than 0.5 mm, more preferably not less than 1 mm, and even more preferably not less than 2 mm;

<24> the method for producing a tertiary amine according to any one of <1> to <21>, wherein a distance between a rectifying section and the adjacent honeycomb catalyst layer in the column reactor is preferably not more than 999 mm, more preferably not more than 499 mm, and even more preferably not more than 199 mm;

<25> the method for producing a tertiary amine according to any one of <1> to <24>, wherein liquid and gaseous raw materials are introduced in the same space, passed through an alleyway, and then supplied to the column reactor;

<26> the method for producing a tertiary amine according to <25>, wherein a ratio of an inner diameter (d1) of the alleyway to a maximum diameter (d2) of a supply route of a mixed phase of the liquid and the gaseous raw materials leading to the alleyway, d1/d2, is preferably within the range of 0.01 to 0.9, more preferably 0.01 to 0.3, and even more preferably 0.03 to 0.3;

<27> the method for producing a tertiary amine according to <25>, wherein a ratio of an inner diameter (d1) of the alleyway to a maximum diameter (d2) of a supply route of a mixed phase of the liquid and the gaseous raw materials leading to the alleyway, d1/d2, is preferably not less than 0.01, more preferably not less than 0.01, and even more preferably not less than 0.03;

<28> the method for producing a tertiary amine according to <25>, wherein a ratio of an inner diameter (d1) of the alleyway to a maximum diameter (d2) of a supply route of a mixed phase of the liquid and the gaseous raw materials leading to the alleyway, d1/d2, is preferably not more than 0.9, and more preferably not more than 0.3;

<29> the method for producing a tertiary amine according to any one of <25> to <28>, wherein a mixed phase of the liquid alcohol and the gaseous primary or secondary amine is preferably supplied at a pressure of 0.005 to 0.9 MPa, more preferably 0.01 to 0.2 MPa, and even more preferably 0.02 to 0.1 MPa in gauge pressure;

<30> the method for producing a tertiary amine according to any one of <25> to <28>, wherein a mixed phase of the liquid alcohol and the gaseous primary or secondary amine is preferably supplied at a pressure of not less than 0.005 MPa, more preferably not less than 0.01 MPa, and even more preferably not less than 0.02 MPa in gauge pressure; and <31> the method for producing a tertiary amine according to any one of <25> to <28>, wherein a mixed phase of the liquid alcohol and the gaseous primary or secondary amine is preferably supplied at a pressure of not more than 0.9 MPa, more preferably not more than 0.2 MPa, and even more preferably not more than 0.1 MPa in gauge pressure.

EXAMPLES

The following Examples demonstrate the present invention. Examples are intended to illustrate the present invention and not to limit the present invention.

In Examples, "%" and "part(s)" refers to "% by mass" and "part(s) by mass", respectively.

Preparation Example 1

Preparation of Film Catalyst

A film catalyst was prepared by fixing a powder catalyst on a film support with a phenol resin as a binder.

A 1 L flask was charged with a synthetic zeolite and then an aqueous solution containing copper nitrate, nickel nitrate, and ruthenium chloride in such amounts as that molar proportions of metal atoms were Cu:Ni:Ru=4:1:0.01. The mixture was heated with stirring. At the temperature of 90° C., an aqueous solution of 10% sodium carbonate was added dropwise to adjust pH to 9 to 10.

The mixture was aged for 1 hour. Then, a precipitate was filtered, washed with water, dried for 10 hours at 80° C., and calcined for 3 hours at 600° C. to obtain the powder catalyst. The powder catalyst contained 50% metal oxides and 50% synthetic zeolite.

To 100 parts of the powder catalyst was added a phenol resin (Sumitomo Bakelite Co. Ltd., PR-9480, nonvolatile matter: 56%) as a binder in such an amount that the nonvolatile matter of the phenol resin was 25 parts. To this was further added 4-methyl-2-pentanone as a solvent in such an amount that the solid matter (the powder catalyst and the nonvolatile matter of the phenol resin) accounted for 57% of the whole mixture.

The mixture was shaken for 30 minutes with a paint shaker (Toyo Seiki Seisaku-sho Ltd., 164.5 g of the catalyst-containing paint and 102 g of 1.0 mm glass beads were fed in a 250 mL plastic container) to obtain a dispersion coating containing the catalyst.

The coating was applied on both surfaces of copper foil (a sheet having dimensions of 6.5 cm by 410 cm and a thickness of 40 μm) as a support with a bar coater, and dried for 1 minute at 130° C.

A half of the dried foil was folded to form a corrugated pattern, white the other half remains flat. The foil was cured for 90 minutes at 150° C. to fix the catalyst in a film shape on both sides of the copper foil. The resultant film catalyst contained solid matters at a weight of 18.75 g per square meter per side excluding the copper foil.

Preparation Example 2

Preparation of Honeycomb Catalyst

A film catalyst prepared as in Preparation Example 1 was used to prepare a honeycomb catalyst.

For a honeycomb catalyst container, used was a stainless steel (SUS304) cylinder having an outer diameter of 27 mm, an inner diameter of 24.2 mm, and a height of 80 mm with a fixed SUS304 mesh bottom having an opening of 5 mm.

Flat and corrugated film catalysts prepared and cured as in Preparation Example 1 were alternately layered and rolled up in a tube, and packed in the container as constructing a honeycomb structure.

Five containers were prepared and vertically stacked in a SUS304 cylinder (column 11) having an inner diameter of 28.0 mm to obtain a column reactor 1.

In a buffer tank 3, 820 g of lauryl alcohol (Kalcol 2098, Kao Corporation) was fed.

Lauryl alcohol was introduced at 9 L/Hr to the column reactor 1 through a pipe having an inner diameter of 6 mm (line 25) connecting to the bottom of the column reactor 1, and circulated between the buffer tank 3 and the column reactor 1.

A metal filter having a hole diameter of 0.025 mm was used as a gas feeder 2. To the column reactor 1 was supplied hydrogen gas at a flow rate of 50 L/Hr, calculated based on the standard state volume, while an inner temperature of the column reactor 1 was elevated to 185° C. The column reactor 1 was allowed to stand at this state for 1 hour to reduce the catalyst. Then, the column reactor 1 was cooled and the lauryl alcohol was removed to obtain a honeycomb catalyst.

Example 1

Production of N-dodecyl-N,N-dimethylamine

A tertiary amine was produced according to the production flow shown in FIG. 1. Cylinders each having an outer diameter of 27 mm, an inner diameter of 24.2 mm, and a length of 30 mm were inserted below the lowest of the five containers (honeycomb catalyst layer 12a in the column container 11) and each between the honeycomb catalyst layers 12a to 12e to provide spaces 13a to 13e in the column reactor 1 used to prepare the honeycomb catalyst in Preparation Example 2.

Perforated plates each having a hole diameter of 3 mm, a thickness of 1 mm, and an aperture ratio of 33% were further fixed in spaces 13a to 13e, as rectifying sections 14a to 14e, at an intermediate portion of each space in the vertical direction, so that each distance from the upper surface of the space to the upper surface of the perforated plate was 14.5 mm, to prepare a column reactor 1 for producing the tertiary amine.

In a buffer tank 3, 820 g of lauryl alcohol was fed. Lauryl alcohol was circulated at a flow rate of 9 L/Hr. A metal filter having a hole diameter of 0.025 mm was used as a gas feeder 2. To the column reactor 1 was supplied hydrogen gas at a flow rate of 25 L/Hr, calculated based on the standard state volume, while the temperature was elevated. The reaction was started by supplying dimethylamine and continued in a cycling system.

A reaction temperature was elevated to 220° C. A supply rate of dimethylamine was adjusted according to the progress of the reaction. A sample of the reaction mixture was periodically taken from the buffer tank 3 and analyzed by gas chromatography to quantify the components from their peak area percentages.

The analysis showed that a time taking to react until an amount of unreacted lauryl alcohol in the reaction mixture reached to 1.0% was 3.8 hours from the start of dimethylamine supply. An integrated amount of dimethylamine supplied was 1.21 molar times the amount of the starting lauryl alcohol. A pressure difference between the entrance and the exit of the column reactor 1 was 0.02 MPa (gauge pressure).

Example 2

The reaction was conducted through the same operations, except that perforated plates each having a hole diameter of 2 mm, a thickness of 1 mm, and an aperture ratio of 40% were used as rectifying sections 14a to 14e instead of plates used in Example 1.

The analysis showed that the reaction took 4 hours from the start of dimethylamine supply to react until an amount of unreacted lauryl alcohol in the reaction mixture reached to 1.0%. An integrated amount of dimethylamine supplied was 1.22 molar times the amount of the starting lauryl alcohol. A pressure difference between the entrance and the exit of the column reactor 1 was 0.02 MPa (gauge pressure).

Example 3

The reaction was conducted through the same operations, except that a liquid and a gas raw materials were together supplied to the column reactor 1 from the bottom through a nozzle having a narrow passage (nozzle 2A shown in FIG. 4(*a*), having a cylindrical shape with an inner diameter ($d_1$) of 1.6 mm, $d_2$ of 4.0 mm, and a length (L) of 5 mm) instead of the gas feeder 2 in Example 1.

The analysis showed that the reaction took 4.1 hours from the start of dimethylamine supply to react until an amount of unreacted lauryl alcohol in the reaction mixture reached to 1.0%. An integrated amount of dimethylamine supplied was 1.16 molar times the amount of the starting lauryl alcohol. A pressure difference between the entrance and the exit of the column reactor 1 was 0.02 MPa (gauge pressure).

Example 4

A honeycomb catalyst container as used in Preparation Example 2 was used. Flat and corrugated film catalysts prepared and cured as in Preparation Example 1 were alternately stacked and rolled up in a tube and installed in the container as constructing a honeycomb structure.

Seven containers were prepared and vertically stacked in an SUS304 cylinder (column 11) having an inner diameter of 28.0 mm. For illustrative purposes, the seven honeycomb catalyst-packed containers were assigned as 12a to 12g, starting from the bottom in accordance with FIG. 1. Spaces and rectifying sections were assigned 13a to 13g and 14a to 14g, starting from the bottom, respectively in the same way.

A perforated plate having a hole diameter of 3 mm, a thickness of 1 mm, and an aperture ratio of 33% was fixed in the inside of each cylinder, as rectifying sections 14a to 14g, in the intermediate of spaces 13a to 13g in the vertical direction such that a distance from the upper surface of the cylinder (column 11) to the upper surface of the perforated plate therein was 14.5 mm to obtain a column reactor 1.

At the bottom of the reactor, the nozzle 2A used in Example 3 was arranged.

Lauryl alcohol at 209° C. at a flow rate of 1.3 L/Hr and hydrogen at a flow rate of 18 L/Hr calculated based on the standard state volume were supplied through the nozzle 2A to react in the reactor.

A sample was taken at the exit of the column reactor during conducting the reaction and analyzed by gas chromatography to quantify components from their peak area percentages.

The analysis showed that a conversion rate of lauryl alcohol to an aldehyde at the exit was 4.6%. A pressure difference between the entrance and the exit of the column reactor was 0.02 MPa (gauge pressure).

This Example showed that N-dodecyl-N,N-dimethylamine could be produced through a production flow containing this reactor instead of the reactor 1 in FIG. 1 or 2 and a buffer tank 3 receiving dimethylamine instead of the reactor 1 in FIG. 1 or 2 and conducting the reactions (i) and (iii) in this rector and the reaction (ii) in the buffer tank 3.

Comparative Example 1

The reaction was conducted through the same operations as in Example 1, except that the column reactor 1 had none of spaces 13a to 13e or none of rectifying sections (perforated plates) 14a to 14e.

The reaction took 4 hours from the start of the reaction until an amount of unreacted lauryl alcohol in the reaction mixture reached to 1.0%. An integrated amount of dimethylamine supplied was 1.43 molar times the amount of the starting lauryl alcohol. A pressure difference between the entrance and the exit of the column reactor 1 was 0.02 MPa (gauge pressure).

Comparative Example 2

The reaction was conducted through the same operations as in Example 1, except that the column reactor 1 had none of rectifying sections (perforated plates) 14a to 14e, but spaces 13a to 13e.

The reaction took 5.0 hours from the start of the reaction until an amount of unreacted lauryl alcohol in the reaction mixture reached to 1.0%. An integrated amount of dimethylamine supplied was 1.28 molar times the amount of the starting lauryl alcohol. A pressure difference between the entrance and the exit of the column reactor 1 was 0.02 MPa (gauge pressure).

Comparative Example 3

Dehydrogenation was conducted through the same operations as in Example 4, except that the column reactor had none of cylinders. The reaction resulted in a conversion rate of lauryl alcohol of 3.7% at the exit of the column reactor 1.

TABLE 1

|  |  | Example | | | Comparative example | |
| --- | --- | --- | --- | --- | --- | --- |
|  |  | 1 | 2 | 3 | 1 | 2 |
| Column reactor | Honeycomb catalyst | Installed | Installed | Installed | Installed | Installed |
|  | Spacer | Installed | Installed | Installed | Not Installed | Installed |
|  | Flow-controlling part | Perforated plate having a hole diameter of 3 mm, a thickness of 1 mm and a rate of opening area of 33% | Perforated plate having a hole diameter of 2 mm, a thickness of 1 mm and a rate of opening area of 40% | Perforated plate having a hole diameter of 3 mm, a thickness of 1 mm and a rate of opening area of 33% | Not installed | Not installed |
|  | Gas supply means | Only gas was supplied through a metal filter | Only gas was supplied through a metal filter | Gas and liquid were supplied together through a nozzle having a narrow passage | Only gas was supplied through a metal filter | Only gas was supplied through a metal filter |
|  | Pressure difference between the pressures at entrance and the exit of the column reactor (MPa) | 0.02 | 0.02 | 0.02 | 0.02 | 0.02 |
| Production of tertiary amine | Time taken until the amount of unreacted lauryl alcohol reached to 1.0% (hr) | 3.8 | 4 | 4.1 | 4 | 5 |
|  | Molar proportion of integrated amount of dimethylamine supplied (to 1 mol of starting alcohol) | 1.21 | 1.22 | 1.16 | 1.43 | 1.28 |

The invention claimed is:

1. A method for producing a tertiary amine through a sequence of reactions of:
   (i) dehydrogenation of an alcohol to produce an aldehyde;
   (ii) addition reaction of a raw material amine to the aldehyde and dehydration to form an imine and/or enamine; and
   (iii) hydrogen reduction of the imine and/or enamine generated by addition reaction and dehydration to produce a tertiary amine,
   wherein reactions (i) and (iii) are conducted in a single column reactor packed with catalyst layers by supplying the alcohol and hydrogen from the bottom of the column reactor,
   and reaction (ii) is conducted in another reactor without the catalyst layers used in the reaction (i) or (iii),
   wherein the column reactor includes two or more honeycomb catalyst layers as the catalyst layers, a space between two or more honeycomb catalyst layers, and rectifying sections for preventing back flow of part or the whole of the raw materials, arranged in the space without contacting with the honeycomb catalyst layer.

2. The method for producing a tertiary amine according to claim 1, wherein an active material used to compose the honeycomb catalyst layer comprises Cu.

3. The method for producing a tertiary amine according to claim 1, wherein the honeycomb catalyst layer has a narrow tubular channel parallel to a flow direction of the reaction fluid.

4. The method for producing a tertiary amine according to claim 1, wherein the rectifying section has several penetrating passages.

5. The method for producing a tertiary amine according to claim 1, wherein the number of honeycomb catalyst layers in the column reactor is not less than 3 stages.

6. The method for producing a tertiary amine according to claim 1, further including a rectifying section for preventing back flow of part or the whole of the raw materials, arranged below the lowest honeycomb catalyst layer without contacting with the honeycomb catalyst layer.

7. The method for producing a tertiary amine according to claim 1, wherein the honeycomb catalyst of the honeycomb catalyst layer in the column reactor is formed by immobilizing a powder catalyst with a binder on the surface of a film support and shaping into a honeycomb structure.

8. The method for producing a tertiary amine according to claim 1, wherein the alcohol is a linear or branched, saturated or unsaturated, aliphatic alcohol having 6 to 36 carbon atoms.

9. The method for producing a tertiary amine according to claim 1, wherein the space in the column reactor has a length of 5 to 1000 mm.

10. The method for producing a tertiary amine according to claim 1, wherein the rectifying section in the column reactor is a perforated plate having a thickness of 0.5 to 20 mm, a hole diameter of 0.5 to 8 mm, and an aperture ratio of 1 to 70%.

11. The method for producing a tertiary amine according to claim 1, wherein a distance between the rectifying section and the honeycomb catalyst layer in the column reactor is 0.5 to 999 mm.

12. The method for producing a tertiary amine according to claim 1, wherein the reaction is conducted under a pressure of 0.013 to 0.3 MPa (absolute pressure) at a temperature of 150 to 300° C. in the column reactor packed with the catalyst layers.

13. The method for producing a tertiary amine according to claim 1, wherein a ratio of the gas supply rate G to a supply rate L ($m^3$/Hr) of a liquid alcohol or a mixture of an alcohol and a reaction product, G/L, is 0.1 to 50.

14. The method for producing a tertiary amine according to claim 1, wherein the alcohol is selected from the group consisting of hexyl alcohol, octyl alcohol, decyl alcohol, lauryl alcohol, myristyl alcohol, palmityl alcohol, stearyl alcohol, behenyl alcohol and oleyl alcohol.

15. The method for producing a tertiary amine according to claim 1, wherein the raw material amine is selected from the group consisting of methylamine, dimethylamine, ethylamine and diethylamine.

16. A method for producing a tertiary amine through a sequence of reactions of:
   (i) dehydrogenation of an alcohol to produce an aldehyde;
   (ii) addition reaction of a raw material amine to the aldehyde and dehydration to form an imine and/or enamine; and
   (iii) hydrogen reduction of the imine and/or enamine generated by addition reaction and dehydration to produce a tertiary amine,
   wherein reaction (i) is conducted in a first column reactor packed with catalyst layers by supplying the alcohol and hydrogen from the bottom of the column reactor,
   wherein reaction (iii) is conducted in a second column reactor packed with catalyst layers,
   and reaction (ii) is conducted in another reactor without the catalyst layers used in the reaction (i) or (iii),
   wherein the first and second column reactors include two or more honeycomb catalyst layers as the catalyst layers, a space between two or more honeycomb catalyst layers, and rectifying sections for preventing back flow of part or the whole of the raw materials, arranged in the space without contacting with the honeycomb catalyst layer.

17. The method for producing a tertiary amine according to claim 16, wherein an active material used to compose the honeycomb catalyst layer comprises Cu.

18. The method for producing a tertiary amine according to claim 16, wherein the honeycomb catalyst layer has a narrow tubular channel parallel to a flow direction of the reaction fluid.

19. The method for producing a tertiary amine according to claim 16, wherein the rectifying section has several penetrating passages.

20. The method for producing a tertiary amine according to claim 16, wherein the number of honeycomb catalyst layers in the first and second column reactors is not less than 3 stages.

21. The method for producing a tertiary amine according to claim 16, further including a rectifying section for preventing back flow of part or the whole of the raw materials, arranged below the lowest honeycomb catalyst layer without contacting with the honeycomb catalyst layer.

22. The method for producing a tertiary amine according to claim 16, wherein the honeycomb catalyst of the honeycomb catalyst layer in the first and second column reactors is formed by immobilizing a powder catalyst with a binder on the surface of a film support and shaping into a honeycomb structure.

23. The method for producing a tertiary amine according to claim 16, wherein the alcohol is a linear or branched, saturated or unsaturated, aliphatic alcohol having 6 to 36 carbon atoms.

24. The method for producing a tertiary amine according to claim 16, wherein the space in the first and second column reactors has a length of 5 to 1000 mm.

25. The method for producing a tertiary amine according to claim 16, wherein the rectifying section in the first and second column reactors is a perforated plate having a thickness of 0.5 to 20 mm, a hole diameter of 0.5 to 8 mm, and an aperture ratio of 1 to 70%.

26. The method for producing a tertiary amine according to claim 16, wherein a distance between the rectifying section and the honeycomb catalyst layer in the first and second column reactors is 0.5 to 999 mm.

27. The method for producing a tertiary amine according to claim 16, wherein the reaction is conducted under a pressure of 0.013 to 0.3 MPa (absolute pressure) at a temperature of 150 to 300° C. in the first and second column reactors packed with the catalyst layers.

28. The method for producing a tertiary amine according to claim 16, wherein a ratio of the gas supply rate G to a supply rate L ($m^3$/Hr) of a liquid alcohol or a mixture of an alcohol and a reaction product, G/L, is 0.1 to 50.

29. The method for producing a tertiary amine according to claim 16, wherein the alcohol is selected from the group consisting of hexyl alcohol, octyl alcohol, decyl alcohol, lauryl alcohol, myristyl alcohol, palmityl alcohol, stearyl alcohol, behenyl alcohol and oleyl alcohol.

30. The method for producing a tertiary amine according to claim 16, wherein the raw material amine is selected from the group consisting of methylamine, dimethylamine, ethylamine and diethylamine.

* * * * *